United States Patent [19]
McInnes et al.

[11] Patent Number: 5,137,513
[45] Date of Patent: Aug. 11, 1992

[54] PERFUSION DILATATION CATHETER

[75] Inventors: Peter R. McInnes, Surrey, England; Vidya J. Nayak; Edward A. Estrada, both of Cupertino, Calif.

[73] Assignee: Advanced Cardiovascular Systems, Inc., Santa Clara, Calif.

[21] Appl. No.: 547,674

[22] Filed: Jul. 2, 1990

[51] Int. Cl.$^5$ .............................................. A61M 29/00
[52] U.S. Cl. ........................................ 604/96; 604/53
[58] Field of Search ............... 604/280, 283, 284, 128, 604/129, 4, 8, 19, 35, 43, 44, 53, 51, 52, 96, 97, 98, 101, 102, 247

[56] References Cited
U.S. PATENT DOCUMENTS

| | | | |
|---|---|---|---|
| 3,889,686 | 6/1975 | Duturbure | 604/102 |
| 3,923,065 | 12/1975 | Nozick et al. | 604/102 |
| 4,821,722 | 4/1989 | Miller et al. | 604/96 |
| 4,857,054 | 8/1989 | Helfer | 604/102 |

Primary Examiner—C. Fred Rosenbaum
Assistant Examiner—Sharon Finkel
Attorney, Agent, or Firm—Crosby, Heafey, Roach & May

[57] ABSTRACT

A perfusion-type intravascular catheter having an outer sheath disposed about the catheter body with a sealing element on the distal end of the sheath to seal off the distal end thereof at a location distal to perfusion ports provided in the wall of the catheter body proximal to an expandable working member such as an inflatable balloon whereby blood can be directed through the proximal perfusion ports into an inner lumen extending through the working member and out of perfusion ports provided into the walls of the catheter distal to the expandable working member to ensure that ischemic conditions do not occur distal to the catheter when the working member is expanded to perform a vascular procedure therein.

11 Claims, 2 Drawing Sheets

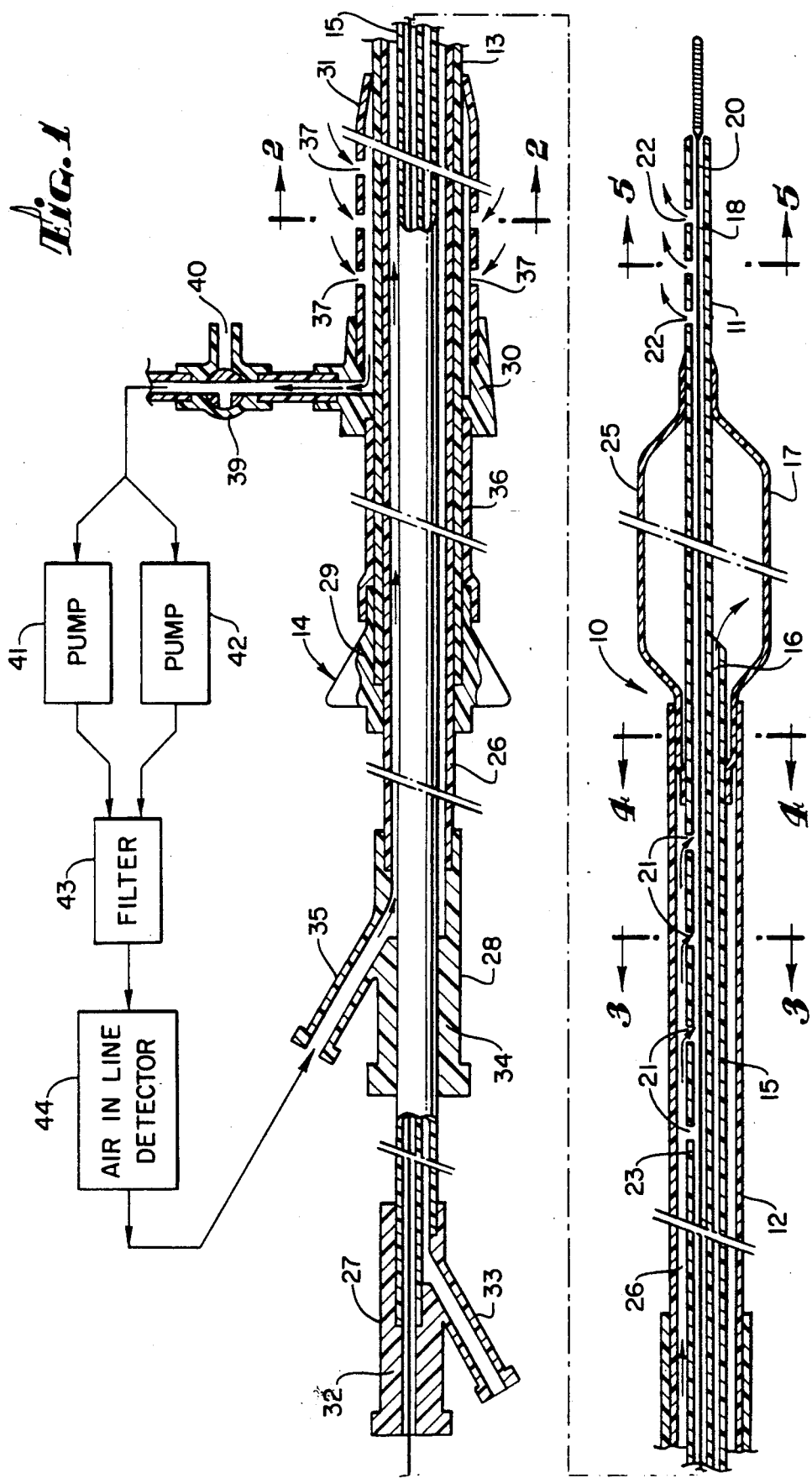

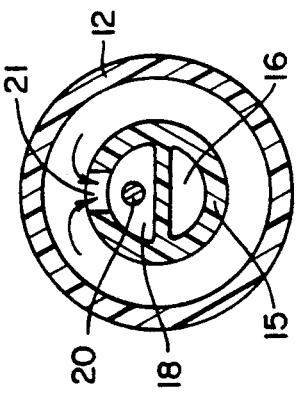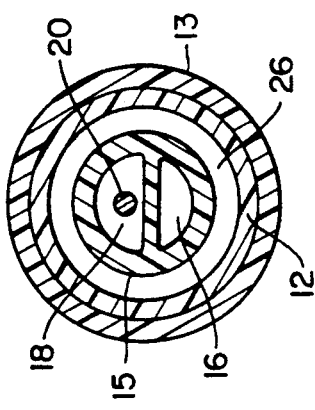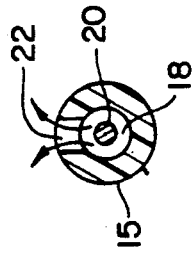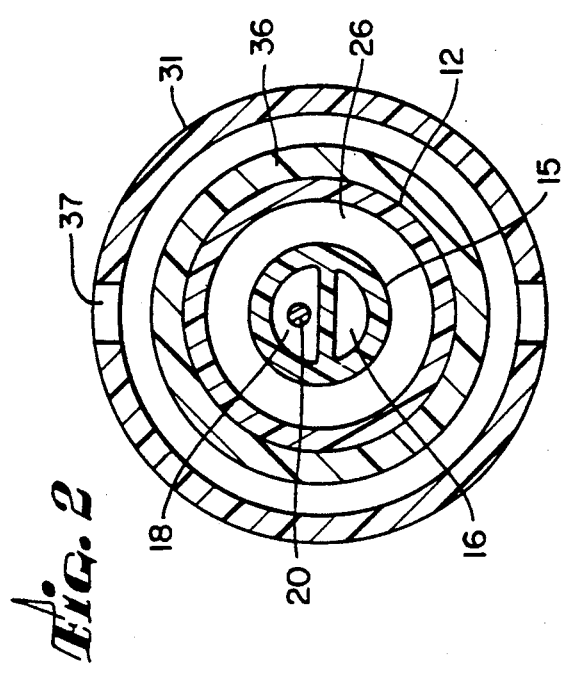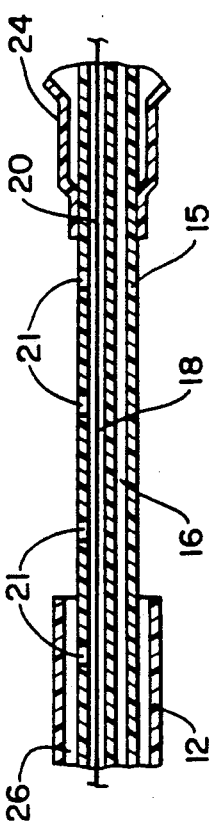

PERFUSION DILATATION CATHETER

BACKGROUND OF THE INVENTION

This invention generally relates to a dilatation catheter for angioplasty procedures such as percutaneous transluminal coronary angioplasty (PTCA).

In PTCA procedures, a dilatation catheter having an inflatable, relatively inelastic balloon on the distal end thereof is advanced through a patient's arterial system until the balloon crosses the atherosclerotic lesion to be dilated. The balloon is inflated to a predetermined size with radiopaque liquid at relatively high pressures (e.g., atmospheres) to dilate the stenotic region and then the balloon is deflated so that the catheter can be removed and blood flow resumed at a higher flow rate due to the expanded diameter of the stenotic region.

Typically a guiding catheter having a preformed distal end is first percutaneously introduced into the patient's arterial system and advanced until the distal tip of the guiding catheter is disposed in the appropriate ostium of the patient's coronary artery. A guidewire is slidably disposed within an inner lumen of a dilatation catheter and both are advanced through the previously positioned guiding catheter to the distal end thereof. The guidewire is first advanced out of the guiding catheter into the patient's coronary anatomy until the distal end of the guidewire crosses the stenotic region to be dilated. The physician usually shapes the distal end of the guidewire to facilitate steering it through the patient's coronary arteries. Once the guidewire is in place, the dilatation catheter is then advanced over the guidewire until the inflatable balloon is positioned within the stenosis. The balloon is inflated to a relatively high pressure to dilate the stenosis and then deflated and removed over the guidewire. For a detailed description of procedures, reference is made to U.S. Pat. No. 4,332,254 (Lundguist), U.S. Pat. No. 4,323,071 (Simpson-Robert), U.S. Pat. No. 4,439,185 (Lundguist), U.S. Pat. No. 4,468,224 (Enzmann et al.), U.S. Pat. No. 4,516,972 (Samson), U.S. Pat. No. 4,538,622 (Samson et al.), U.S. Pat. No. 4,554,929 (Samson et al.), U.S. Pat. No. 4,569,347 (Frisbie), U.S. Pat. No. 4,571,240 (Samson et al.), U.S. Pat. No. 4,638,805 (Powell), U.S. Pat. No. 4,748,982 (Horzewski et al.), all of which are hereby incorporated herein in their entirety by reference thereto.

The prior art has shown dilatation and other intravascular catheters which perfuse blood through the interior of a balloon when the balloon is inflated during angioplasty or other intravascular procedure in order to avoid ischemic conditions distal to the inflated balloon during the procedure. For example, intravascular catheters providing perfusion capabilities are described in U.S. Pat. No. 3,834,394 (Hunter et al), U.S. Pat. No. 4,423,725 (Baran et al.) and U.S. Pat. No. 4,790,315 (Mueller, Jr. et al.) which are incorporated herein by reference thereto. See also, U.S. Pat. No. 4,581,017 (Sahota). However, the catheters described in these references rely on the natural blood flow through the artery to perfuse blood through the balloon and distal to the catheter and as a result these catheters do not always provide sufficient blood to tissue distal to the catheter to completely avoid ischemic conditions, particularly with long term dilatation, e.g. an hour or more.

Gruntzig et al. in U.S. Pat. No. 4,195,637 describes pumping blood from an extracorporeal source through the inner lumen of a dilatation catheter. In the catheter system described, the blood is delivered through the proximal end of the catheter in a construction which would require the complete removal of the guidewire when perfusing blood. However, complete removal of the guidewire while the catheter remains within the stenosis is not very desireable from a clinical point of view.

What has been needed and heretofore unavailable is a perfusion-type dilatation catheter which can easily and quickly perfuse blood distal to the catheter with sufficient pressure and flow rate to avoid ischemic conditions distal to the catheter. The present invention satisfies this need.

SUMMARY OF THE INVENTION

The present invention is directed to a catheter for performing intravascular procedures, such as angioplasty, which can perfuse blood distal to the catheter when the vascular procedure partially or completely blocks the vascular passageway.

An intravascular catheter of the present invention generally includes an elongated catheter body with a working member on the distal portion thereof which expands during the vascular procedure and reduces blood flow through the blood vessel. The catheter body has an tubular member with an inner lumen which extends through the expandable working member. Perfusion ports pass through the walls thereof both proximally and distally to the expandable working member and are in fluid communication with the inner lumen.

An outer sheath is disposed about the catheter body defining therebetween an annular passageway. Means are provided to seal off the distal end of the sheath about the catheter body distal to the perfusion ports located proximal to the expandable working member. In a preferred embodiment the working member is a balloon which has a proximal portion with a smaller inflated diameter than the inflated diameter of the working section of the balloon. This smaller diameter proximal balloon portion is disposed within the distal end of the sheath so that upon the inflation of the balloon this proximal portion expands within and seals off the distal end of the sheath.

Means such as one or more pumps are provided to supply oxygenated blood to the annular passageway between the sheath and the catheter body under a fluid pressure higher than the pressure in the blood vessel. In this manner blood can be driven from the annular passageway through the proximal perfusion ports into the inner lumen, distally through the inner lumen and then out of the perfusion ports distal to the working member. When the working member is expanded thereby impeding flow through the vascular passageway, the blood flow through the inner lumen of the catheter will be adequate to prevent ischemic conditions.

Oxygenated blood for perfusion is conveniently withdrawn from the patient's artery by means of an introducer shaft which is employed to percutaneously introduce the guiding and other catheters into the patient's artery. The introducer shaft has one or more parts through which oxygenated blood can be aspirated. Pumping means withdraws blood through a side arm of an adapter on the proximal end of the introducer and pumps the withdrawn blood to the side arm of an adapter which is mounted on the proximal end of the sheath. Blood is directed through this side arm into and through the annular passageway between the sheath and the exterior of the catheter body. The blood flows from the annular passageway through the proximal perfusion ports into the inner lumen within the catheter body and then out the distal perfusion ports to supply the oxygenated blood to tissue distal to the catheter. Suitable safeguards should be provided when withdrawing oxygenated blood from the patient to avoid aspirating air which might form an embolism within the patient's coronary or other artery. Additionally, care must be exercised to control the blood pressure within reasonable limits to avoid injury to the blood vessel walls distal to the catheter. The blood flow through the inner lumen of the catheter body is controlled independent of the natural blood pressure in the artery to ensure that sufficient amounts of oxygenated blood are provided to the tissue distal to the catheter.

These and other advantages of the invention will become more apparent from the following detailed descriptions thereof when taken in conjunction with the accompanying exemplary drawings.

BRIEF DESCRIPTION OF THE DRAWINGS

FIG. 1 is a schematic elevational view, partially in section, of a dilatation catheter embodying features of the invention;

FIG. 2 is a transverse cross-sectional view taken along the lines 2—2 as shown in FIG. 1;

FIG. 3 is a transverse cross-sectional view taken along the lines 3—3 as shown in FIG. 1;

FIG. 4 is a transverse cross-sectional view taken along the lines 4—4 as shown in FIG. 1;

FIG. 5 is a transverse cross-sectional view taken along the line 5—5 as shown in FIG. 1;

FIG. 6 is a sectional elevational view of the part of the catheter of FIG. 1 containing the proximal perfusion ports showing the sheat partially overlying those ports.

DETAILED DESCRIPTION OF THE INVENTION

Reference is made to FIG. 1 which schematically illustrates a perfusion dilatation catheter assembly 10 embodying features of the invention. The catheter assembly 10 generally includes a dilatation catheter 11, an overlying sheath 12 disposed about the dilatation catheter, a guiding catheter 13 and an adapter assembly 14 on the proximal end of the catheter assembly. The dilatation catheter 11 includes an elongated catheter body 15 with a first inner lumen 16 extending therein for directing inflation fluid from the proximal end of the catheter body 10 to the interior of the expandable balloon 17 on the distal end thereof, and a second inner lumen 18 which is extends through the length of the catheter body to the distal end thereof and which is adapted to slidably receive a guidewire 20. A plurality of proximal perfusion ports 21 and distal perfusion ports 22 pass through the wall 23 of the catheter body 15 and are in fluid communication with the second inner lumen 18. The inflatable balloon 17 has a proximal section 24 which has a smaller inflated diameter than that of the working section 25 thereof.

The sheath 12 is an elongated tube which is disposed about the catheter body 15 and defines therewith a lumen 26. The distal end of the sheath 12 extends over the smaller diameter proximal section 24 of the balloon 17 so that upon the inflation of the balloon the proximal section inflates to seal the distal end of the sheath 12. In this manner, blood passing through the lumen 26 is forced to flow through the proximal perfusion ports 21 and the portion of the second inner lumen 18 which extends through the interior of the balloon 17 and then out of the distal perfusion ports 22. The distal section of guidewire 21 may be pulled back through the second lumen 18 to a location proximal to the perfusion port 22 so as to not reduce blood flow through the lumen.

The adapter assembly 14 on the proximal end of the catheter assembly 10 includes a first adapter 27 which is secured to the proximal end of catheter body 15, a second adapter 28 which is secured to the proximal end of the sheath 12, a third adapter 29 which is secured to the proximal end of the guiding catheter 13 and a fourth adapter 30 which is secured to the proximal end of an introducer 31.

Guidewire 20 passes through hemostatic valve (not shown) provided in arm 32 of adapter 27. Inflation fluid is introduced through side arm 33 of adapter 27 into the first inner lumen 16 of the catheter body 15 by suitable means such as a syringe (not shown). The catheter body 15 passes through arm 34 of second adapter 28 attached to the proximal end of the sheath 12. Oxygenated blood is directed through side arm 35 of adapter 28 into the lumen 26 between the catheter body 15 and the sheath 12. The catheter body 15 should be at least 5 cm, preferably at least 10 cm longer than the sheath 12 so that there can be relative longitudinal movement therebetween which will be discussed hereinafter. The sheath 12 passes through the proximal end of third adapter 29 which is secured to the proximal end of the guiding catheter 13. A short outer tubular member 36 is provided on the exterior of the guiding catheter 13 to tightly fit into the proximal end of the fourth adapter 30 which is secured to the introducer 31 to thereby seal the proximal end of the guiding catheter 13 within the introducer 30.

The shaft of the introducer 31 is provided with a plurality of entry ports 37 along its length to allow oxygenated blood to be aspirated from the patient's artery through the side arm 38 thereof. Valve 39 is provided in side arm 38 to allow priming fluid to be introduced through conduit 40 and introducer 31 to initiate the aspiration.

Oxygenated blood from the patient's artery is aspirated through the side arm 38 by the action of pumps 41 and 42 which preferably are positive displacement such as those having reciprocating pistons pumps and which are controlled to operate in sequential cycles, i.e., one pump fills with blood while the other is discharging blood, so that there is a continuous level of elevated of pressure through the filter 43 and air-in-line detector 44. The introducer 31, side arm 38 and the lines to the pumps 41 and 42 should be primed with fluid before the actuation of the pumps. The filter 43 and the air-in-line detector 44 are provided to ensure that thrombus-free and air-free blood is redirected back to the patient. Model 1500 infusion pumps manufactured and sold by the IVAC Corporation have been found to be particularly suitable for use within this system. An IBM AT personal computer has been used to control the sequencing of the pumping cycles so that positive pressure is maintained downstream of the pumps and negative pressure is maintained upstream of the pump to avoid the loss of the prime.

While in the presently preferred embodiment oxygenated blood is withdrawn from the same artery into which the assembly 10 is introduced, other sources for the blood can be employed. For example, the blood can be removed from arteries of the patient not involved with the procedure.

The components of the perfusion catheter assembly 10 can be made from a wide variety of conventional materials. The catheter body and sheath can be made of polyethylene tubing, the balloon from polyethylene or polyethylene terephthalate. The core member of the guidewire may be stainless steel or nitinol and the coil on the distal end thereof made of highly radiopaque metals such as platinum, palladium, tungsten, rhenium, gold and alloys and composites thereof. The dimensions of the various component parts of the catheter assembly for coronary angioplasty are generally about the same size as conventional angioplasty catheters, except that the outer sheath increases the overall profile of the catheter somewhat. Angioplasty catheters for peripheral arteries tend to have larger dimensions because the arteries into which they are usually inserted are larger that coronary arteries.

The catheter assembly 10 is operated in the following manner. The shaft of introducer 31 is percutaneously introduced into the patient's femoral artery using a conventional Seldinger technique. Guiding catheter 13 is inserted through the proximal end of the adapter 30 of the introducer 31 and advanced through the patient's femoral and illiac arteries, the abdominal aorta, the aortic arch and into the vicinity of the ostium of the desired coronary artery. The proximal end of the guiding catheter 13 is torqued to seat the preshaped distal tip thereof properly within the ostium of the desired coronary artery.

Once the distal tip of the guiding catheter 13 is properly seated, the dilatation catheter 11, with a guidewire 20 preloaded therein, is introduced into the proximal end of the sheath 12 and advanced therein until the balloon 17 extends out of the distal end of the sheath. This assembly is introduced into the proximal end of adapter 29 and advanced through the guiding catheter 13 which is disposed within the patient until it reaches the distal end of the guiding catheter. The guidewire 20 is first advanced out of the distal end of the guiding catheter 13 and into the patient's coronary artery until it crosses the location for the vascular procedure such as a stenotic region for a balloon angioplasty procedure. The dilatation catheter 11 is then advanced over the guidewire 20 until the working section 25 of the expandable balloon 17 is disposed within the stenotic region. Sheath 12 is then advanced over the catheter body 15 until the distal end of the sheath extends over the proximal section 24 of balloon 17. The dilatation catheter 11 should be at least 5 cm, preferably at least 10 cm longer than the sheath 12 so that the dilatation catheter can be first positioned with its balloon 17 across the stenosis and then the sheath can be advanced into a position with its distal tip extends over the inflatable proximal portion 24 of the balloon 17.

Inflation fluid is directed through side arm 33 of the adapter 27 and into the inner lumen 16 of the catheter body 15 wherein the inflation fluid flows to the interior of the balloon 17 to inflate the balloon and dilate the stenosis. Inflation of the balloon 17 causes the proximal section 24 thereof to expand and press against the inner surface of the distal end of the sheath 12 to thereby seal the distal end thereof.

Preferably, the working section 25 of the balloon 17 has a length longer than the stenosis and an inflated diameter approximately the same as the natural diameter of the blood vessel, so that when the balloon is inflated the entire stenosis is dilated but the balloon does not inflate beyond the natural diameter of the blood vessel at that location in order to minimize damage to the arterial wall.

Oxygenated blood is withdrawn from the patient's femoral artery (or other artery into which the assembly 10 is introduced) by aspiration through the ports 37 in the shaft of introducer 31 by the action of the pumps 41 and 42. The introducer 31 and adapter 30 and the lines to the pumps 41 and 42 are primed with a suitable fluid prior to the initiation of pumping action. Pumping action of the reciprocating pistons of pumps 41 and 42 are alternately cycled to provide a constant positive pressure in the discharge line to filter 43 and to ensure no loss in the prime. The blood passes though filter 43 to remove any undesirable particulate or thrombi and through the air-in-line detector 44 to ensure that no air emboli are pumped back through the catheter assembly 10 into the patient's vascular system.

The blood from the air-in-line detector 44 flows through the side arm 35 and through lumen 26 disposed between the catheter body 15 and the sheath 1 to the proximal ports 21 in the catheter body 15. With the distal end of the sheath 12 being sealed by the inflated proximal section 24 of the balloon 17, the blood is caused to pass through the proximal ports 21, through the second lumen 18 and out the distal perfusion ports 23.

The system of the present invention provides considerably more blood to tissue distal to the inflated balloon 17 than that prior perfusion systems which rely on natural blood flow. The balloon of the present system can be inflated for an extended period (e.g. from a few minutes up to twenty-four hours or more) without ischemic conditions being generated distal to the balloon. However, care must be exercised to ensure that the pressure distal to the catheter is not at an excessively high level which might cause injury to the arterial wall. Upon the completion of the vascular procedure the balloon 17 is deflated and the catheter assembly removed from the patient.

The present invention has been described herein in terms of certain preferred embodiments. For example, the sheath 12 is shown to be sealed by the inflatable proximal section 24 of balloon 17. It will be readily apparent to those skilled in the art that other sealing means can be employed. An elastomeric sealing element can be positioned on the inner wall of the sheath 12 or on the outer surface of the catheter body 15 to seal off the distal end of the sheath. Other modifications and improvements can be made to the present invention without departing from the scope thereof.

What is claimed is:

1. A perfusion catheter for performing a procedure within a patient's vascular system, comprising:
    a) an elongated catheter body having proximal and distal ends, a working member proximally adjacent the distal end thereof which partially or completely occludes a blood vessel when performing a vascular procedure therein and a inner lumen which extends through the catheter body and which is adapted to slidably receive a guidewire;
    b) at least one proximal perfusion port in the catheter body located proximal to the working member and at least one distal perfusion port in the wall of the catheter body distal to the working member, the perfusion ports being in fluid communication with the inner lumen adapted to receive a guidewire;

c) an elongated tubular sheath which is disposed about the catheter body and forms a lumen therebetween:
d) means to seal the distal end of the sheath about the catheter body distal to proximal perfusion ports; and
e) means to pump blood from a source thereof through the lumen between the catheter body and the sheath, through the proximal perfusion ports into the inner lumen and out distal perfusion ports.

2. The perfusion catheter of claim 1 wherein the working member is an expandable balloon suitable for dilating a stenosis.

3. The perfusion catheter of claim 2 wherein an inflation lumen extends through the catheter body from the proximal end thereof to the interior of the balloon.

4. The perfusion catheter of claim 2 wherein the balloon has a distal working cylindrical portion for dilating a stenosis and a proximal cylindrical portion with an inflated diameter smaller than the inflated diameter of the working portion of the balloon which is adapted to fit within the distal end of the sheath so that when the balloon is inflated the proximal cylindrical portion seals the distal end of the sheath.

5. The perfusion catheter of claim 1 wherein an adapter assembly is provided on the proximal end of the catheter body to direct blood under pressure through the lumen defined between the sheath and the catheter body.

6. The perfusion catheter of claim 5 wherein the adapter assembly includes a means to withdraw blood from the blood vessel into which the catheter assembly is introduced.

7. The perfusion catheter of claim 6 wherein the means to withdraw blood is an introducer shaft having at least one entry port therein.

8. A method of perfusing blood through an intravascular catheter while performing a vascular procedure within a patient's blood vessel comprising:
a) providing a perfusion catheter assembly comprising
an elongated catheter body having proximal and distal ends, a working member proximally adjacent the distal end thereof which partially or completely occludes a blood vessel when performing a vascular procedure thereon and an inner lumen which extends through the catheter body and which is adapted to slidably receive a guidewire,
at least one proximal perfusion port in the wall of the catheter body located proximal to the working member and at least one distal perfusion port in the catheter body distal to the working member, the perfusion ports being in fluid communication with the inner lumen adapted to receive a guidewire,
an elongated tubular sheath which is disposed about the catheter body and forms a lumen therebetween,
means to seal the distal end of the sheath about the catheter body distal to proximal perfusion ports, and
means to pump blood from a source thereof through the lumen between the catheter body and the sheath, through the proximal perfusion ports into the inner lumen and out distal perfusion ports;
b) advancing the catheter assembly distally through the patient's blood vessel until the working member is located at a desired location within the blood vessel;
c) sealing the distal end of the sheath at a location distal to the proximal perfusion ports in the catheter body;
d) performing a vascular procedure within the blood vessel which reduces blood flow therethrough; and
e) pumping blood through the lumen between the catheter body and the sheath, through the proximal perfusion ports into the second lumen, and out distal perfusion ports to avoid ischemic conditions distal to the catheter.

9. The method of claim 8 wherein the working member is an expandable balloon which is expanded to dilate a stenosis in the blood vessel.

10. The method of claim 8 wherein the catheter assembly is percutaneously introduced into the patient's femoral artery and blood for perfusion is withdrawn through a lumen in an introducer shaft used to introduce a guiding catheter into the patient's femoral artery.

11. The method of claim 8 wherein the pumping means includes at least two positive displacement pumps having reciprocating pistons which are arranged in parallel and are operated in sequentially so that a continuous high pressure output therefrom is obtained.

* * * * *